United States Patent [19]

Misner

[11] Patent Number: 5,463,060
[45] Date of Patent: Oct. 31, 1995

[54] ONE-POT PROCESS

[75] Inventor: Jerry W. Misner, Indianapolis, Ind.

[73] Assignee: Eli Lilly and Company, Indianapolis, Ind.

[21] Appl. No.: 886,800

[22] Filed: May 21, 1992

[51] Int. Cl.$^6$ .................................................. C07D 457/02
[52] U.S. Cl. .................................................. 546/68
[58] Field of Search ................................................ 546/68

[56] References Cited

U.S. PATENT DOCUMENTS

| | | | |
|---|---|---|---|
| 4,166,182 | 8/1979 | Kornfeld et al. | 546/67 |
| 4,782,152 | 11/1988 | Misner | 546/67 |

OTHER PUBLICATIONS

Hutchins et al., *J. Org. Chem.*, 38(10), 1961–62 (1973).
Kametani et al., *J. Med. Chem.*, 12, 694–96 (1969).
Sommer et al., *J. Org. Chem.*, 36(6), 824–28 (1971).
Shamma et al., *Tet. Let.*, (13), 1375–79 (1966).
Manoharan et al., *Synthesis*, 809–12 (1983).

*Primary Examiner*—Gary L. Geist
*Assistant Examiner*—Catherine Scalzo
*Attorney, Agent, or Firm*—Roger S. Benjamin; Joseph A. Jones

[57] ABSTRACT

Pergolide is produced from 8,9-dihydroelymoclavine by a one-pot process in which it is reacted successively with 1-iodopropane, with a sulfonyl halide, and with an alkali metal thiomethoxide without isolation of intermediate products.

20 Claims, No Drawings

ONE-POT PROCESS

BACKGROUND OF THE INVENTION

Pergolide, as disclosed in U.S. Pat. No. 4,166,182 of Kornfeld and Bach, is a well-known drug particularly useful for the treatment of Parkinson's disease. The present invention provides a quick and economical process for the synthesis of pergolide in high purity and excellent yield, making use of safe and easily obtainable ingredients. The invention belongs to the fields of organic and pharmaceutical chemistry.

While the invention provides exceptionally good economy of starting and intermediate compounds, and provides a high yield of pure product, its most particular advantage lies in the avoidance of the isolation of intermediates, which are difficult to contain and present hazards in handling and processing. Thus, an important advantage in safety to the operators and the environment of the process is provided by the use of the present invention.

SUMMARY OF THE INVENTION

This invention provides a one-pot process for preparing pergolide comprising reacting 8,9-dihydroelymoclavine with 1-iodopropane at elevated temperature in the presence of a calcium, magnesium or alkali metal bicarbonate or carbonate and a solvent chosen from N-methylpyrrolidinone, hexamethylphosphoramide, dimethylpropyleneurea and dimethylethyleneurea until the 8,9-dihydroelymoclavine is substantially consumed to prepare a first intermediate mixture; diluting the first intermediate mixture with a large volume of a basic solvent chosen from pyridine, picoline and lutidine, chilling the diluted mixture to a low temperature, combining it with a toluene- or $C_1$–$C_3$ alkanesulfonyl halide, and allowing reaction to continue at low temperature until the first intermediate is substantially consumed to prepare a second intermediate mixture; combining the cold second intermediate mixture with a cold solution of alkali metal thiomethoxide, and allowing reaction to continue at elevated temperature until the second intermediate is substantially consumed to prepare a crude pergolide mixture; diluting the crude pergolide mixture with water to obtain solid pergolide, and washing the pergolide with water to obtain pergolide of at least 90% purity.

DESCRIPTION OF THE PREFERRED EMBODIMENTS

In the present invention, all amounts, proportions, ratios and the like, are expressed in weight units, unless otherwise stated. All temperatures are expressed in °C.

The present process begins with 8,9-dihydroelymoclavine which was disclosed by Kornfeld and Bach in U.S. Pat. No. 4,166,182. It is presently sold by Gedeon Richter of Budapest, Hungary, and by Kawaken Fine Chemicals Co., Ltd., Tokyo, Japan.

The process is carried out by reacting the starting compound with 1-iodopropane to prepare the first intermediate, then reacting the first intermediate with a toluene- or $C_1$–$C_3$ alkanesulfonyl halide to form the second intermediate, and then reacting that intermediate with an alkali metal thiomethoxide to prepare pergolide, which is isolated and purified by simple washing with water. The process is shown in outline form by the following scheme.

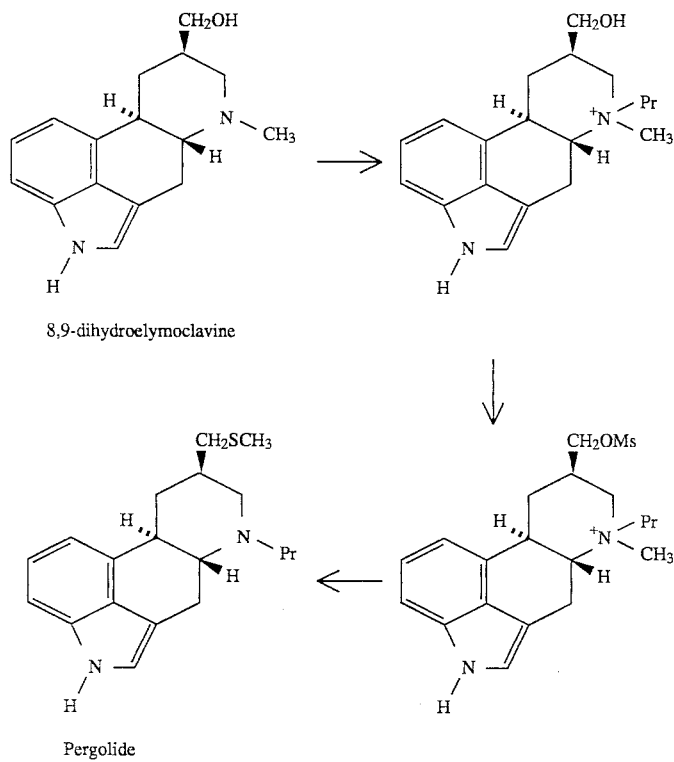

As pointed out above, the first and second intermediates are not isolated, but the successive reactions are carried out by mere additions of reagents to the successive intermediate mixtures.

The process is begun by combining the starting material, a small excess of 1-iodopropane, the bicarbonate or carbonate, and the solvent, of which N-methylpyrrolidinone is preferred, in a reaction vessel of appropriate size. Excess amounts of 1-iodopropane in the range of from about 1.05 to about 2 equivalents, most preferably about 1.1 to about 1.3 equivalents, are used, but only a small amount of the base, such as from about 0.01 to about 0.3 equivalents, is used. The preferred base is sodium carbonate, but calcium, magnesium, sodium, potassium and lithium bicarbonates and carbonates are also appropriate.

Only a modest volume of the solvent is necessary, since the reaction at this stage can be quite concentrated. For example, when N-methylpyrrolidinone is used, only about 1–4 volumes, compared to the volume of 8,9-dihydroelymoclavine, most preferably about 2 volumes, are necessary.

The reaction vessel should be kept under an inert atmosphere, such as dry nitrogen, and the reaction mixture is warmed to an elevated temperature, such as from about 50° to about 100°, most preferably from about 65° to about 85°. The reaction mixture is held at elevated temperature, preferably with stirring, until the starting material is substantially all consumed, which, typically, takes from about 3 to about 5 hours at about 75°. Progress of the reaction may be monitored by chromatography, making use of nitrile-treated silica columns eluted with aqueous acetonitrile buffers. Most preferably, the reaction is allowed to continue until about 99% of the starting material has disappeared, as measured by chromatography.

When the reaction has gone to the desired degree of completion, the reaction mixture is cooled to a temperature below 30°. While the next step of the process may be carried out immediately, it is not necessary, because the first intermediate is quite stable. Thus, the first intermediate mixture may be stored, under an inert atmosphere at room temperature, for as long as several weeks before the rest of the process is carried out.

The first intermediate mixture is diluted with a large volume of pyridine, picoline or lutidine, still under an inert atmosphere. The volume of basic solvent should be in the range of from about 3 volumes to about 10 volumes, based on the volume of solvent in the first intermediate mixture. Most preferably, from about 4 to about 7 volumes, especially about 5 volumes, of the basic solvent is used. The preferred basic solvent is pyridine. The diluted intermediate mixture is then cooled to a low temperature in the range of from about −50° to about 0°, most preferably about −10°. While the temperature is maintained, and certainly is not allowed to rise above about 0°, the sulfonyl halide is slowly added. The most preferred halide is methanesulfonyl chloride, but any of the toluene-, methane-, ethane-, and n-propanesulfonyl bromides, chlorides and iodides may be used, especially chlorides, and more especially the $C_1$–$C_2$ alkanesulfonyl chlorides. A substantial excess of the halide is used, most preferably about 2.5 equivalents, but in the range of from about 1.5 to about 5 equivalents.

Because of the low temperature requirement, the addition of sulfonyl halide must be slow, and most of the reaction in the second intermediate mixture occurs while the addition is being made. Thus, it is usually found that only about 1 to 3 hours of additional reaction time after the completion of the addition is necessary to obtain substantially complete consumption of the first intermediate. Progress of the reaction may be followed by chromatography as above.

The second intermediate is not particularly stable, and so the second intermediate mixture should not be stored more than 1 or 2 days before the final step of the process is carried out. If the second intermediate must be stored, it should be at a low temperature as described above.

The second intermediate is converted to pergolide by reaction with sodium, potassium or lithium thiomethoxide. A large excess of the thiomethoxide is used, in the range of from about 5 to about 15 equivalents, based on the amount of the starting compound. It is preferred to use from about 8 to about 14 equivalents, most preferably about 12 equivalents. It is convenient to prepare the thiomethoxide in situ, by the reaction of methanethiol with an alkali metal methoxide, which reaction is readily carried out, preferably at a low temperature as described above. If the thiomethoxide is prepared in situ, it is important to use a small to moderate excess of methanethiol, to assure that no methoxide remains to enter the reaction mixture.

The reaction is not injured by the presence of water, so the thiomethoxide can be added as an aqueous solution, most conveniently in an aqueous solvent, or in a dry organic solvent. The solvent may preferably be the same solvent used in the first intermediate mixture, or may be chosen from the amides, such as dimethylformamide and dimethylacetamide, the ethers, such as tetrahydrofuran, the alkanols, and other water-miscible solvents.

The thiomethoxide solution is combined at low temperature with the cold second intermediate mixture, both of them at low temperature as defined above, but most preferably at a temperature about −10°. The addition of one to the other is carried out under a controlled rate to maintain the temperature of the final mixture below ambient temperature. When the addition is complete, the temperature is allowed to rise, and the mixture may be heated immediately to an elevated temperature as defined above, most preferably about 80°. Depending on the concentration of the reaction mixture, it may be necessary to add more solvent to permit good agitation of the mixture. The reaction is allowed to continue until the second intermediate is substantially consumed and converted to pergolide, which requires a few hours, such as about 1 to 4 hours, at about 80°, but, of course, requires longer times at lower temperatures as is usually observed with organic reactions. The progress of the final reaction may be followed by chromatography as above.

When the second intermediate has been consumed, and the desired degree of completion of the reaction has been obtained, the crude pergolide mixture is diluted with water. Only a moderate volume of water is needed, most preferably from about 1 to about 1.5 times the volume of the crude pergolide mixture, but the amount is not particularly important since pergolide is substantially insoluble in water. The pergolide precipitates immediately, and is washed in the usual manner, separated from the wash water, and additionally washed to obtain substantially pure pergolide, at least 90% pure by chromatographic analysis.

Pergolide is marketed and used as a pharmaceutical in the form of its methanesulfonate. When the present one-pot process is complete, the pergolide product of it is preferably purified by chromatography, and then is converted to the methanesulfonate salt, ready for pharmaceutical use, as shown in U.S. Pat. No. 4,782,152 of Misner.

The present invention is further explained by the following examples, in order to assure that the reader fully understands the invention.

The following example further illustrates the operation of the present invention, to assure that the reader can successfully carry out the invention.

EXAMPLE

First Intermediate

To a stirred flask were added 12.8 g of 8,9-dihydroelymoclavine (Kawaken), 10.6 g of 1-iodopropane, 0.42 g of anhydrous sodium carbonate, and 25 ml of molecular sieve-dried N-methylpyrrolidinone. A nitrogen atmosphere was maintained over the mixture while it was stirred and heated to 75°.

The reaction was allowed to continue at constant temperature for about 18 hours, and was then analyzed by liquid chromatography on a Zorbax CN column, eluting with 4:1 methanol:0.1M ammonium acetate, using a 290 nm detector. (Zorbax CN is obtained from DuPont). No 8,9-dihydroelymoclavine was detected in the reaction mixture, illustrating complete conversion to the first intermediate.

The reaction mixture, about 39 ml in volume, was divided into five equal aliquots for further experiments.

Second Intermediate

One of the aliquots of the first intermediate mixture obtained above was combined under dry nitrogen with 39 ml of molecular sieve-dried pyridine in a 100 ml flask equipped with a nitrogen inlet, ice bath, thermometer and stirrer. The solution was chilled to 0°, and 2.86 g of methanesulfonyl chloride was added dropwise, taking care that the temperature of the reaction mixture did not exceed 5°. The addition time was about 8 minutes.

The reaction mixture was monitored by liquid chromatography as explained in the step above, and it was found after one hour of stirring at about 0° that the mixture contained 5.9% of the first intermediate. After two and a half hours, the content of the first intermediate was down to about 4%, and the reaction mixture was advanced to the next step of the process.

Sodium Thiomethoxide

Thirty ml of molecular sieve-dried N-methylpyrrolidinone was added under a nitrogen blanket to a flask, and was chilled to −5°. Then 6.2 ml of methanethiol and 4.0 g of powdered sodium hydroxide were added. The temperature of the mixture immediately rose to 5°, and the mixture was cooled and stirred for one hour, maintaining the temperature at about −2°.

Pergolide

To the above mixture was added the second intermediate mixture, allowing the temperature to rise exothermically to 21°. The mixture was stirred at ambient temperature for 15 minutes and was then heated to 80° and stirred at that temperature for 2 hours. The reaction was then quenched by the addition of 60 ml of water, and the aqueous mixture was cooled to 5° and filtered. The solid was washed with 60 ml of water, and dried in a vacuum oven at 50° overnight. Analysis of the dried solid showed that it was 94.1% pure pergolide. The yield was 2.86 g, equivalent to 90.8% yield, based on the starting 8,9-dihydroelymoclavine.

I claim:

1. A one-pot process for preparing pergolide comprising reacting 8,9-dihydroelymoclavine with 1-iodopropane at elevated temperature in the presence of a calcium, magnesium or alkali metal bicarbonate or carbonate and a solvent chosen from N-methylpyrrolidinone, hexamethylphosphoramide, dimethylpropyleneurea and dimethylethyleneurea until the 8,9-dihydroelymoclavine is substantially consumed to prepare a first intermediate mixture; diluting the first intermediate mixture with a large volume of a basic solvent chosen from pyridine, picoline and lutidine, chilling the diluted mixture to a low temperature, combining it with a toluene- or $C_1$–$C_3$ alkanesulfonyl halide, and allowing reaction to continue at low temperature until the first intermediate is substantially consumed to prepare a second intermediate mixture; combining the cold second intermediate mixture with a cold solution of alkali metal thiomethoxide, and allowing reaction to continue at elevated temperature until the second intermediate is substantially consumed to prepare a crude pergolide mixture; diluting the crude pergolide mixture with water to obtain solid pergolide, and washing the pergolide with water to obtain pergolide of at least 90% purity.

2. A process of claim 1 wherein an alkali metal bicarbonate or carbonate is present in the first intermediate mixture.

3. A process of claim 1 wherein the solvent is N-methylpyrrolidinone in the first intermediate mixture.

4. A process of claim 1 wherein the basic solvent is pyridine in the second intermediate mixture.

5. A process of claim 1 wherein the sulfonyl halide is a sulfonyl chloride in the second intermediate mixture.

6. A process of claim 5 wherein the sulfonyl halide is a $C_1$–$C_2$ alkanesulfonyl chloride in the second intermediate mixture.

7. A process of claim 2 wherein the solvent is N-methylpyrrolidinone in the first intermediate mixture.

8. A process of claim 3 wherein an alkali metal bicarbonate or carbonate is present in the first intermediate mixture.

9. A process of claim 3 wherein the basic solvent is pyridine in the second intermediate mixture.

10. A process of claim 4 wherein the sulfonyl halide is a sulfonyl chloride in the second intermediate mixture.

11. A process of claim 4 wherein the alkali metal thiomethoxide is sodium thiomethoxide in the pergolide mixture.

12. A process of claim 7 wherein the basic solvent is pyridine in the second intermediate mixture.

13. A process of claim 8 wherein the sulfonyl halide is a sulfonyl chloride in the second intermediate mixture.

14. A process of claim 9 wherein an alkali metal bicarbonate or carbonate is present in the first intermediate mixture.

15. A process of claim 10 wherein the alkali metal thiomethoxide is sodium thiomethoxide in the pergolide mixture.

16. A process of claim 1 wherein the alkali metal thiomethoxide is sodium thiomethoxide in the pergolide mixture.

17. A process of claim 16 wherein the solvent is N-methylpyrrolidinone in the first intermediate mixture.

18. A process of claim 17 wherein the basic solvent is pyridine in the second intermediate mixture.

19. A process of claim 18 wherein the sulfonyl halide is a sulfonyl chloride in the second intermediate mixture.

20. A process of claim 19 wherein sodium carbonate is present in the first intermediate mixture.

* * * * *